US006613552B1

(12) United States Patent
Frost et al.

(10) Patent No.: US 6,613,552 B1
(45) Date of Patent: *Sep. 2, 2003

(54) BIOCATALYTIC SYNTHESIS OF SHIKIMIC ACID

(75) Inventors: John W. Frost, Okemos, MI (US); Karen M. Frost, Okemos, MI (US); David R. Knop, Okemos, MI (US)

(73) Assignee: Board of Trustees operating Michigan State University, East Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/240,440

(22) Filed: Jan. 29, 1999

(51) Int. Cl.$^7$ .............................. C12P 7/40; C12P 7/00; C12P 7/42; C12N 15/70; C12N 1/20

(52) U.S. Cl. ...................... 435/136; 435/132; 435/146; 435/69.1; 435/172.3; 435/252.3; 435/252.33; 435/320.1; 435/471; 536/23.2

(58) Field of Search ................................ 435/136, 69.1, 435/132, 172.3, 252.3, 320.1, 252.33, 146, 471; 536/23.2

(56) References Cited

U.S. PATENT DOCUMENTS

| | | | |
|---|---|---|---|
| 5,168,056 A | 12/1992 | Frost | |
| 5,906,925 A | 5/1999 | Liao | |
| 6,436,664 B1 * | 8/2002 | Iomantas et al. | 435/41 |

FOREIGN PATENT DOCUMENTS

| | | |
|---|---|---|
| WO | 94 14955 | 7/1994 |
| WO | 96 34961 | 11/1996 |

OTHER PUBLICATIONS

Weaver, L. et al., J. Bacter., vol. 172, No. 11, pp. 6581–6584, Nov. 1990.*

Attwood, T., Science, vol. 290, No. 5491, pp. 471–473, Nov. 1990.*

Brown, K.D. et al., "Transport And Utilization Of The Biosynthetic Intermediate Shikimic Acid In *Escherichia coli,*" *Biochim. Biophys. Acta* 428:550–562 (1976).

Draths, K.M. et al., "Biocatalysis And Nineteenth Century Organic Chemistry: Conversion Of D–Glucose Into Quinoid Organics," *J. Am. Chem. Soc.* 114(24):9725–9726 (1992).

Draths, K.M. et al., "Environmentally Compatible Synthesis Of Catechol From D–Glucose," *J. Am. Chem. Soc.* 117:2395–2400 (1995).

Dell, K.A. et al., "Identification And Removal Of Impediments To Biocatalytic Synthesis Of Aromatics From D–Glucose: Rate–Limiting Enzymes In The Common Pathway Of Aromatic Amino Acid Biosynthesis," *J. Am. Chem. Soc.* 115:11581–11589 (1993).

Haslem, E., "Chemistry Of Intermediates In The Common Pathway," *Shikimic Acid: Metabolism and Metabolites,* Wiley & Sons, New York, pp. 40–42 (1993).

Kim. C.U. et al., "Influenza Neuraminidase Inhibitors Possessing A Novel Hydrophobic interaction In The Enzyme Active Site: Design, Synthesis, And Structural Analysis Of Carbocyclic Sialic Acid Analogues With Potent Anti–Influenza Activity," *J. Am. Chem. Soc.* 119:681–690 (1997).

Konstaninov, K.B. et al., "Glucose Feeding Strategy Accounting For The Decreasing Oxidative Capacity Of Recombinant *Escherichia coli* In Fed–Batch Cultivation For Phenylalamine Production," *J. Ferment. Bioeng.* 70:253–260 (1990).

Konstantinov, K.B. et al., "Physiologically Motivated Strategies For Control Of The Fed–Batch Cultivation Of Recombinant *Escherichia coli* For Phenylalanine Production," *J. Ferment. Bioeng.* 71:350–355 (1991).

Mitsuhashi, S. et al., "Aromatic Biosynthesis—XIII. Conversion Of Quinic Acid To 5–Dehydroquinic Acid By Quinic Dehydrogenase," *Biochim. Biophys. Acta* 15:268–280 (1954).

Pittard, J. et al., "Gene Controlling The Uptake Of Shikimic Acid By *Escherichia coli,*" *J. Bacteriol.* 92:1070–1075 (1966).

Rohloff, J.C. et al., "Practical Total Synthesis Of The Anti–Influenza Drug GS–4104," *J. Org. Chem.* 63:4545–4550 (1998).

Tan, D.S. et al., "Stereoselective Synthesis Of Over Two Million Compounds Having Structural Features Both Reminiscent Of Natural Products And Compatible With Miniaturized Cell–Based Assays," *J. Am. Chem. Soc.* 120:8565–8566 (1998).

EP 99 95 6926 Supplementary European Search Report.

* cited by examiner

Primary Examiner—Rebecca E. Prouty
Assistant Examiner—Delia Ramirez
(74) Attorney, Agent, or Firm—Harness, Dickey & Pierce, P.L.C.

(57) ABSTRACT

A bioengineered synthesis scheme for the production of shikimic acid from a carbon source is provided. Methods of producing shikimic acid from a carbon source based on the synthesis scheme are also provided.

42 Claims, 2 Drawing Sheets

BIOCATALYTIC SYNTHESIS OF SHIKIMIC ACID

SPONSORSHIP

Work on this invention was sponsored in part by the United States Department Of Agriculture Grant No. 95-37500-1930 and the National Science Foundation Grant No. CHE963368 amendment 002. The Government may have certain rights in the invention.

FIELD OF THE INVENTION

The present invention is related to the production of shikimic acid and more specifically, to methods of producing shikimic acid from bioconversion of a carbon source.

BACKGROUND OF THE INVENTION

Shikimic acid is an attractive chiral synthon with its highly functionalized; six-membered carbocyclic ring and multiple asymmetric centers. A metabolic intermediate of aromatic amino acid biosynthesis, shikimic acid has emerged as an essential chiral starting material in the synthesis of neuraminidase inhibitors effective in the treatment of influenza. Kim. C. U. et al., *J. Am. Chem. Soc.* 119:681 (1997); Rohloff, J. C. et al., *J. Org. Chem.* 63:4545 (1998). Chiral, as well as aromatic chemicals, can also be synthesized from shikimic acid. For example, acid catalyzed dehydration of shikimic acid affords p-hydroxybenzoic acid (Eykmann, J. F., *Ber. Dtch. Chem. Ges.* 24:1278 (1891)). p-Hydroxybenzoic acid, which has an annual production of $7 \times 10^6$ kg, is the key precursor to parabens and a monomer used in the synthesis of liquid crystal polymers. Shikimic acid has also recently been used as the starting point for synthesis of a large combinatorial library of molecules. Tan, D. S. et al., *J. Am. Chem. Soc.* 120:8565 (1998).

Shikimic acid is obtained via tedious multi-step isolation procedures from plants. Unfortunately, current isolation of shikimic acid from the fruit of Illicium plants (Haslem, E., *Shikimic Acid: Metabolism and Metabolites*, Wiley & Sons, New York, pp. 40–42 (1993)) precludes its use in kilogram-level synthesis.

Therefore, it would be desirable to provide a method to produce large quantities of shikimic acid. It would also be desirable if such a method were cost-efficient, using inexpensive starting materials. It would further be desirable if the method employed non-toxic compounds and was environmentally benign.

SUMMARY OF THE INVENTION

A bioengineered synthesis scheme for production of shikimic acid from a carbon source is provided. In one embodiment, the bioconversion methods of the present invention comprise the microbe-catalyzed conversion of a carbon source to shikimic acid. As shown in the synthesis scheme of FIG. 1, the microbe-catalyzed conversion step of the present invention requires four enzymes which may be provided by a recombinant microbe. In a preferred embodiment, the recombinant microbe is *Escherichia coli* designed to cause reduction of 3-dehydroshikimate to shikimic acid and to inhibit any further conversion of shikimic acid along the aromatic amino acid biosynthetic pathway.

The biocatalytic synthesis method for shikimic acid provided herein, is believed to be environmentally benign, economically attractive, and utilizes abundant renewable sources as a starting material, Additional objects, advantages, and features of the present invention will become apparent from the following description and appended claims, taken in conjunction with the accompanying drawing.

BRIEF DESCRIPTION OF THE DRAWINGS

The various advantages of the present invention will become apparent to one skilled in the art by reading the following specification and subjoined claims and by referencing the following drawing in which:

DETAILED DESCRIPTION OF THE PREFERRED EMBODIMENTS

A bioengineered synthesis scheme for the production of shikimic acid from a carbon source is provided herein. Methods of producing shikimic acid from a carbon source based on the synthesis scheme are also provided.

In one embodiment, a method is provided wherein the carbon source is converted to shikimic acid by a recombinant microbe. Manipulation of the common aromatic amino acid biosynthetic pathway of the microbe results in a significant production of shikimic acid when the recombinant microbe is cultured in the presence of a carbon source. The carbon source is converted to 3-deoxy-D-arabino-heptulosonate-7-phosphate (DAHP) which is subsequently converted by 3-dehydroquinate synthase to 3-dehydroquinate (DHQ) which is then dehydrated to 3-dehydroshikimate (DHS) by 3-dehydroquinate dehydratase (c, FIG. 1). 3-dehydroshikimate is converted to shikimic acid by shikimate dehydrogenase (d, FIG. 1). Metabolism of shikimic acid may be prevented by blocking or impeding shikimate kinase activity (e,f, FIG. 1), thus allowing for the accumulation of significant amounts of shikimic acid. In a preferred embodiment, the microbe will be unable to reabsorb shikimic acid from the medium due to a mutation in shikimate uptake (shiA). Thus, once formed, shikimic acid can not be converted into quinic acid or any other molecule in the pathway.

The bioconversion methods of the present invention are carried out under conditions of time, temperature, pH, nutrient type and concentration, aeration conditions, and controlled glucose concentrations, to provide maximal conversion of the carbon source to shikimic acid. As described in detail in the Specific Examples, in a preferred embodiment, a fed-batch fermentor is used to convert the carbon source to shikimic acid, followed by isolation of the shikimic acid from the fermentation broth by ion-exchange chromatography. The batch fermentor process and chromatography methods are known to those skilled in the art.

As used herein, the phrase "carbon source" is meant to include biomass derived carbon sources including, but not limited to, xylose, arabinose, glycerol, glucose and the intermediates in the Krebs cycle (e.g., dicarboxylic acids), either alone or in combination. In a preferred embodiment, the carbon source is glucose. The carbon source may be derived from renewable resources such as, without limitation, corn, sugar beets and sugar cane.

In another embodiment, the recombinant microbe employed in the methods of the present invention is *E. coli*. In a preferred embodiment, the *E. coli* comprises an aroB cassette inserted into the serA locus and disruption of the aroL and aroK loci (e and f, FIG. 1). This recombinant *E. coli* may further comprise a plasmid carrying aroF$^{FBR}$, aroE and serA gene inserts. Shikimic acid accumulates due to the absence of the aroL- and aroK-encoded isozymes of shikimate kinase while the second copy of aroB increases the catalytic activity of 3-dehydroquinate synthase. Dell, K. A. et al., *J. Am. Chem. Soc.* 115:11581 (1993). It will be appreciated, however, that the aroL and aroK loci mutations are not essential and are employed to provide greater production of shikimic acid.

In a preferred embodiment, the recombinant *E. coli* comprises plasmid pKD12.112 carrying aroF$^{FBR}$, serA and aroE inserts. The aroF$^{FBR}$ gene insert encodes a mutant 3-deoxy-D-arabino-heptulosonate-7-phosphate synthase isozyme (a, FIG. 1) insensitive to feedback inhibition by aromatic amino acids or other aromatic molecules which increases carbon flow into the common aromatic amino acid biosynthetic pathway. Amplified shikimate dehydrogenase resulting from expression of aroE compensates for the enzyme's feedback inhibition by shikimic acid. Pittard, J. et al., *J. Bacteriol.* 92:1070 (1966); Brown, K. D. et al., *Biochim. Biophys. Acta.* 428:550 (1976). Due to a mutation in the *E. coli* genomic serA locus required for L-serine biosynthesis, growth in minimal salts medium and plasmid maintenance follows from expression of plasmid-localized serA. The plasmid serA insert thus allows microbial growth in minimal salts medium, distinguishing the microbes.

In another embodiment, the *E. coli* comprises plasmid pKD12.138. This plasmid is derived from and carries the same gene inserts as pKD12.112 as well as a tktA gene insert encoding for transketolase. Transketolase catalyzes formation of D-erythrose 4-phosphate, an unstable aldose phosphate typically maintained at vanishingly low concentrations in the cell. Elevated expression of transketolase provides additional D-erythrose 4-phosphate for subsequent condensation with phosphoenolpyruvate to form 3-deoxy-D-arabino-heptulosonate-7-phosphate, the first committed intermediate of aromatic amino acid biosynthesis.

In another embodiment, the aroF$^{FBR}$, serA and/or aroE genes are inserted directly into the genome of the host cell. Thus a plasmid would not be required for the production of shikimic acid from such a recombinant microbe.

Examples of the above-described preferred recombinant microbes of the present invention, *E. coli* SP1.1/pKD12.112, SP2.1/pKD12.112, SP1.1/pKD12.138 and SP2.1/pKD12.138 are described in Specific Example 1 and have been deposited with the American Type Culture Collection (ATCC), 10801 University Boulevard, Manassas, Va. 20110-2209, under the terms of the Budapest Treaty, and accorded the ATCC designation numbers 98905, 98903, 207055 and 207054, respectively. The deposit will be maintained in the ATCC depository, which is a public depository, for a period of 30 years, or 5 years after the most recent request, or for the effective life of a patent, whichever is longer, and will be replaced if the deposit becomes depleted or nonviable during that period. Samples of the deposit will become available to the public and all restrictions imposed on access to the deposit will be removed upon grant of a patent on this application.

The following table sets forth the four enzymes required for the conversion of glucose to shikimic acid, the genes encoding same and the origin of the genes in the exemplary recombinant microbes of the present invention.

TABLE 1

| Enzyme† | Gene (origin) |
|---|---|
| a) 3-deoxy-D-arabino-heptulosonic acid 7-phosphate synthase | aroF$^{FBR}$ (plasmid) |
| b) 3-dehydroquinate synthase | aroB (additional copy inserted into genome) |
| c) 3-dehydroquinate dehydratase | aroD (genome) |
| d) 3-dehydroshikimate dehydrogenase | aroE (plasmid) |

Figure 1:
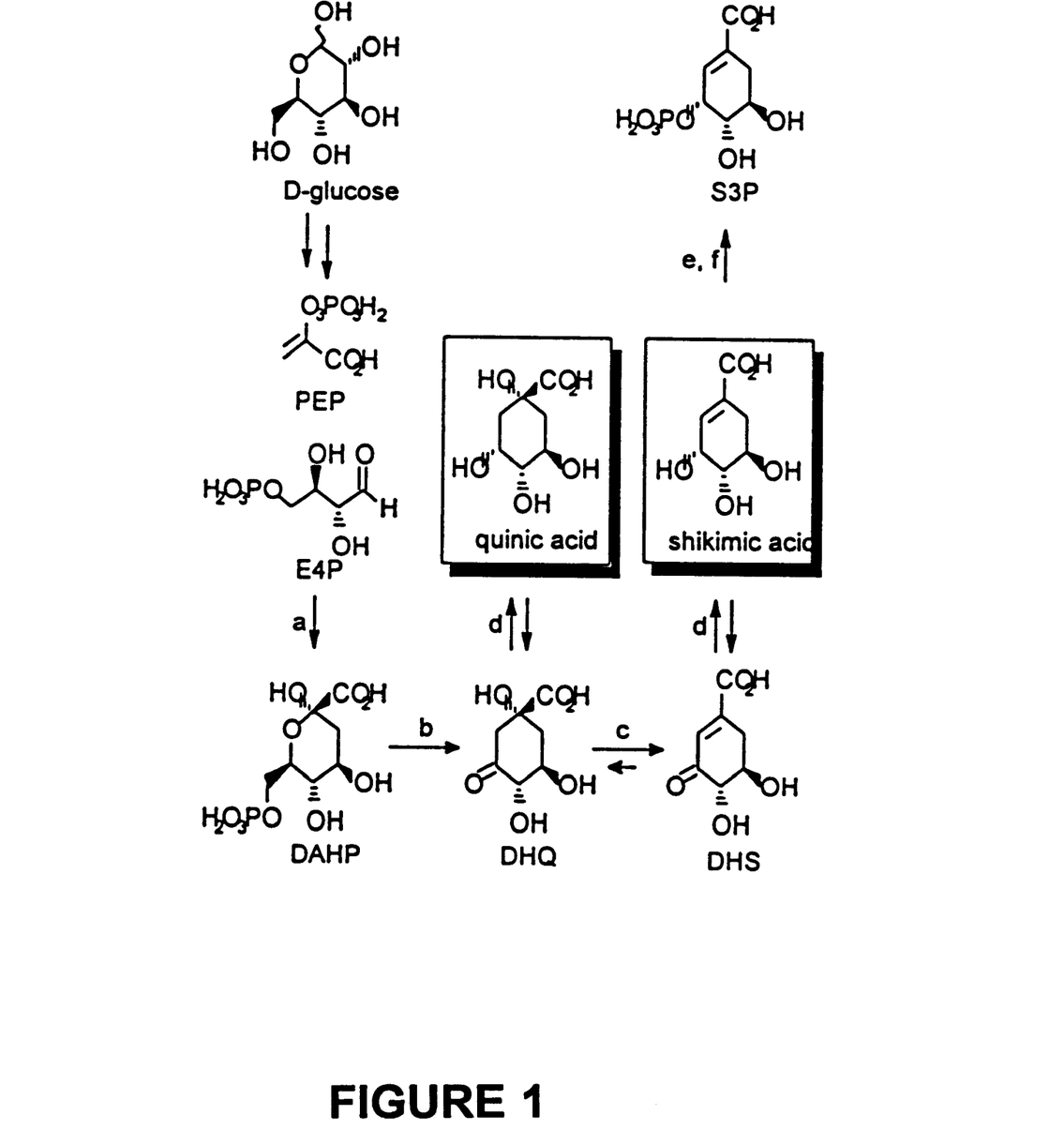
FIG. 1 is a schematic illustrating the bioengineered synthesis scheme of the present invention for producing shikimic acid.

†Enzymes a)-d) correspond to a-d of FIG. 1.

Although *E. coli* is specifically described herein as the microbe for carrying out the methods of the present invention, it will be appreciated that any microorganism such as the common types cited in the literature and known to those skilled in the art, may be employed, provided the microorganism can be altered to effect the desired conversion, e.g., carbon source to shikimic acid. Thus, it is envisaged that many types of fungi, bacteria and yeasts will work in the methods of the present invention. Such microorganisms may be developed, for example, through selection, mutation, and/or genetic transformation processes with the characteristic and necessary capability of converting one constituent of the synthesis scheme of the present invention to another. Methods for such development are well known to the skilled practitioner.

In order to carry out the bioconversion methods of the present invention, a solution containing a carbon source is contacted with the recombinant microbe to form a bioconversion mixture which is maintained under appropriate conditions to promote the conversion of the carbon source to the desired constituent, e.g., shikimic acid. In a preferred embodiment, the bioconversion mixture is maintained at a temperature of about 30° C. to about 37° C. and a pH of about 6.5 to about 7.5. It is preferred that the bioconversion mixture also contain other substances necessary to promote the viability of the recombinant microbes such as mineral salts, buffers, cofactors, nutrient substances and the like. The bioconversion mixture is preferably maintained under glucose limited conditions. In a preferred embodiment, the rate of glucose addition is determined by the level of dissolved oxygen concentration. A preferred steady state over the course of fermentation is about 100 to about 200 μmol glucose or a dissolved oxygen concentration of about 5% to about 35% air saturation.

The more general requirements for the maintenance of viability of microorganisms are well known and specific requirements for maintaining the viability of specific microorganisms are also well known as documented in the literature, or are otherwise easily determined by those skilled in the art. The shikimic acid may then be recovered from the bioconversion mixture by methods known in the art (e.g., ion-exchange chromatography) and further purified by recrystallization.

Culturing of the recombinant microbes of the present invention produce not only shikimic acid, but can also produce quinic acid in the fermentation broth. If the quinic acid concentration is too high, it is difficult to purify the shikimic acid away from the quinic acid. In a preferred embodiment, the molar ratio of shikimic acid to quinic acid in the fementor broth is such that shikimic acid can be purified away from quinic acid. Preferably, the molar ratio will be greater than about 9. More preferably, the molar ratio will be greater than about 20 and most preferably, it will be greater than about 40.

In one embodiment, the molar ratios of shikimic acid to quinic acid in the fermentor broth are controlled by controlling the concentration of the carbon source during fermentation. While not wishing to be bound by theory, it is thought that at lower carbon source concentrations, shikimic acid in the fermentor broth is taken back up by the cells as an alternate carbon source and converted to quinic acid which is then secreted back into the fermentation broth. Increasing the concentration of the carbon source during fermentation inhibits this uptake of shikimic acid and lowers or eliminates the contaminating quinic acid. As a non-limiting example, increasing the glucose concentration by increasing the $K_c$ from 0.1 to 0.8 and thus increasing the rate of addition of a 65% (w/v) glucose solution during fermentation of SP1.1/pKD12.112, resulted in an increase in the molar ratio of shikimic acid to quinic acid from 3.0 to 12.0.

In another embodiment, the molar ratio of shikimic acid to quinic acid is controlled by addition of non-metabolizable (non-hydrolyzable) glucose analogs to the fermentation medium. Preferably, the glucose analog is methyl glucopyranoside present at a concentration of between about 0.1 mM and about 10 mM. More preferably, it is present in a concentration of between about 0.5 and about 1.0 mM. The methyl glucopyranoside may be methyl-α-glucopyranoside, methyl-β-glucopyranoside, or a mixture thereof. Because these analogs are non-hydrolyzable, they may be added only at the beginning of fermentation.

In order to more fully demonstrate the advantages arising from the present invention, the following example is set forth. It is to be understood that the following is by way of example only and is not intended as a limitation on the scope of the invention.

SPECIFIC EXAMPLE 1

Creation of Plasmids and Host Strains

Two host strains created for shikimic acid biosynthesis originated from two different *E. coli* strains. *E. coli* SP1.1 was created from RB791, a strain which differs from wild-type W3110 by only a single mutation. A second shikimate-producer, *E. coli* SP2.1, was created from a strain possessing several characterized and an unknown number of uncharacterized mutations. SP2.1 was created from AB2848, an isolate of several rounds of chemical mutagenesis originally selected for a mutation in the dehydroquinate dehydratase-encoding aroD gene. Creation of two organisms for shikimic acid biosynthesis allowed evaluation of the effect of various culture parameters in different genomic backgrounds.

Creation of SP1.1 began with insertion of aroB into the serA locus of RB791 via homologous recombination. This event led to an *E. coli* with increased dehydroquinate synthase expression while inactivating expression of phosphoglycerate dehydrogenase, an enzyme necessary for de novo serine biosynthesis. Subsequent P1-mediated transduction of aroL478::Tn10 and aroK17::$Cm^R$ from *E. coli* AL0807 afforded SP1.1 in which both isozymes of shikimate kinase are inactive. Creation of SP2.1 proceeded similarly but required the additional step of reintroduction of dehydroquinate dehydratase activity to the organism. After insertion of aroB into the serA locus of AB2848, P1-mediated transduction of a functional copy of aroD into the genome afforded an organism capable of aromatic amino acid biosynthesis but not serine biosynthesis. Subsequent P1-mediated transduction of aroL478::Tn10 and aroK17::$Cm^R$ from *E. coli* AL0807 afforded SP2.1.

Plasmid pKD12.112 is a pSU18-based vector (approximately 15 to 20 copies per cell) that contains genes encoding a feedback insensitive isozyme of 3-deoxy-D-arabino-heptulosonate-7-phosphate synthase (aroF$^{FBR}$), shikimate dehydrogenase (aroE), phosphoglycerate dehydrogenase (serA), and β-lactamase (Ap$^R$). Expression of aroF$^{FBR}$, serA, and β-lactamase proceed from their respective native promoters while aroE expression occurs from both its native promoter (designated P$_{aroE}$) and from the strong hybrid promoter tac (P$_{tac}$). Increased expression of a feedback insensitive isozyme of 3-deoxy-D-arabino-heptulosonate-7-phosphate synthase increases the percentage of metabolites directed into shikimate biosynthesis while increased shikimate dehydrogenase expression reduces the impact of this enzyme's inhibition by shikimic acid, thereby reducing byproduct dehydroshikimate formation. Inclusion of serA on pKD12.112 forces host strains SP1.1 and SP2.1 to maintain the plasmid in culture medium lacking serine supplementation. Finally, inclusion of the β-lactamase gene provides additional means of selective pressure for plasmid maintenance in SP1.1 and SP2.1. Resistance to ampicillin, however, was utilized only as a secondary selective pressure during preparation of fermentation inoculants. Ampicillin was never added to fermentation cultures.

Plasmid pKD12.138 was prepared from pKD12.112 by insertion of transketolase-encoding tktA. Transketolase catalyzes formation of D-erythrose 4-phosphate, an unstable aldose phosphate typically maintained at vanishingly low concentrations in the cell. Elevated expression of transketolase provides additional D-erythrose 4-phosphate for subsequent condensation with phosphoenolpyruvate to form 3-deoxy-D-arabino-heptulosonate-7-phosphate, the first committed intermediate of aromatic amino acid biosynthesis. Increased transketolase expression improves both the rate of formation and the final titer of shikimic acid.

SPECIFIC EXAMPLE 2

Synthesis of Shikimic Acid from Glucose

I. Results

Culturing SP1.1/pKD12.112 for 42 h with $K_c$=0.1 resulted in the synthesis of 27.2 g/L of shikimic acid, 12.6 g/L of quinic acid, and 4.4 g/L of 3-dehydroshikimic acid (DHS). DHS accumulation reflected the expected feedback inhibition of shikimate dehydrogenase by shikimic acid. Draths, K. M. et al., *J. Am. Chem. Soc.* 114:9725 (1992). By contrast, quinic acid biosynthesis was surprising given the absence in *E. coli* of quinic acid dehydrogenase which catalyzes 3-dehydroquinate and quinic acid interconversion. DHS was readily removed by heating the fermentor broth to convert DHS into protocatechuic acid which was absorbed by activated carbon during decolorization. Unfortunately, quinic acid contamination was in excess of what could be purified away from shikimic acid by crystallization.

Minimizing the cytosolic concentration of 3-dehydroquinic acid appeared to be a reasonable strategy for reducing quinic acid contamination of the shikimic acid synthesized by *E. coli* SP1.1/pKD12.112. The aroD gene encoding 3-dehydroquinate dehydratase was consequently localized on plasmid pKD12.152A along with aroE, aroF$^{FBR}$ and serA. However, attendant amplified expression of 3-dehydroquinate dehydratase did not reduce the levels of quinic acid contamination in the shikimic acid synthesized by SP1.1/pKD12.152A underfed-batch fermentor conditions identical to those employed for SP1.1/pKD12.112. While not wishing to be bound by theory, these results suggest that quinic acid formation may not result from de novo biosynthesis but rather from equilibration of initially synthesized shikimic acid.

Figure 2:
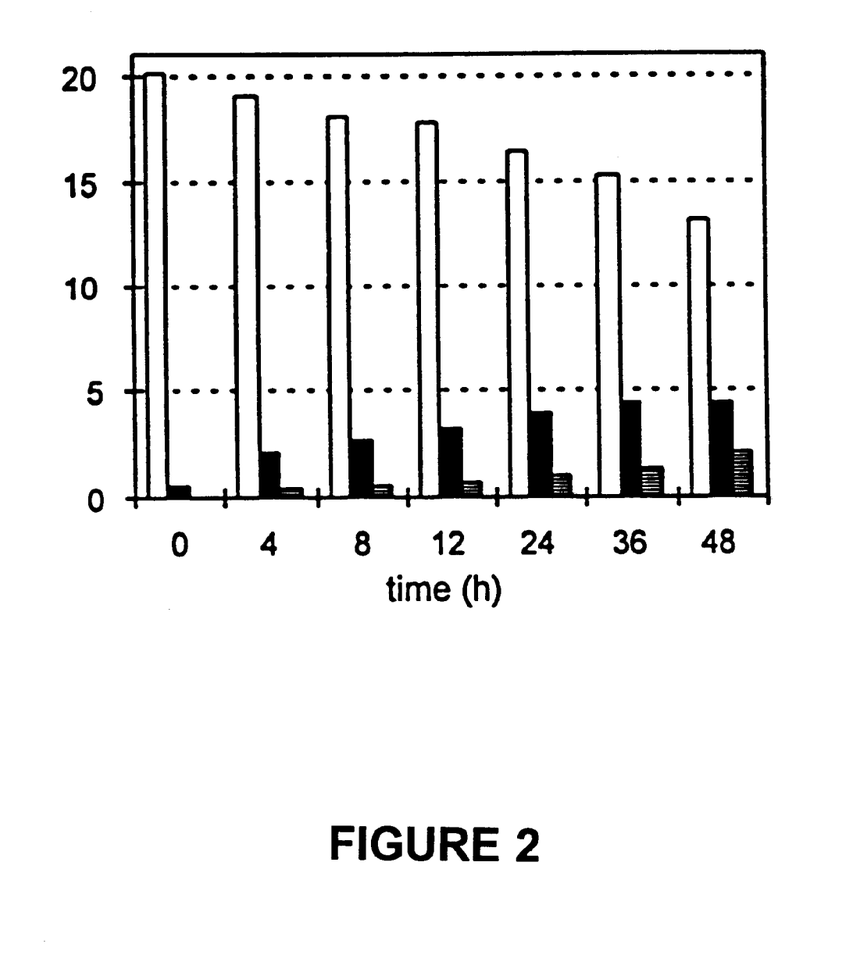
FIG. 2 is a graph showing the equilibrium of shikimic and quinic acids catalyzed by SP1.1/pKD12.112.

Equilibration of quinic and shikimic acids has previously been examined in cell-free extracts of *Klebsielia pneumoniae*. Mitsuhashi, S. et al., *Biochim. Biophy. Acta* 15:268 (1954). To be relevant to quinic acid formation in *E. coli* SP1.1/pKD12.112, the common pathway must be able to operate in vivo in the reverse of its normal biosynthetic direction. To test this possibility, SP1.1/pKD12.112 cells collected from the fermentor after 24 h were washed, resuspended in fresh minimal salts medium containing shikimic acid, and then shaken. Formation of quinic acid (solid bars, FIG. 2) and 3-dehydroshikimic acid (hatched bars, FIG. 2) along with a corresponding decrease in shikimic acid concentration (open bars, FIG. 2) indicated that SP1.1/pKD12.112 can catalyze formation of quinic acid from initially synthesized shikimic acid.

The possible role of shikimic acid transport from the culture medium into the microbial cytoplasm during observed equilibration pointed to a strategy for minimizing quinic acid contamination. Shikimic acid transport (Pittard, J. et al., *J. Bacteriol.* 92:1070 (1966); Brown, K. D. et al., *Biochim. Biophys. Acta* 428:550 (1976)) in *E. coli* may be an evolutionary vestige of a previous ability to catabolize shikimic and quinic acids as sole sources of carbon for growth and metabolism. Since utilization of nonglucose carbon sources is often subject to catabolite repression, increasing D-glucose availability might repress shikimic acid transport thereby minimizing formation of quinic acid.

The rate of D-glucose addition, and thus D-glucose availability, in all fermentation runs was controlled by the proportional-integral-derivative (PID) setting gain ($K_c$). For example, synthesis by *E. coli* SP1.1/pKD12.112 of the mixture of shikimic and quinic acids (Table 2) employed a PID setting of $K_c$=0.1. Increasing glucose availability by increasing the PID setting to $K_c$=0.8 resulted (Table 2) in a drastic reduction in the formation of quinic acid throughout the entire fermentation. After 42 h of cultivation, *E. coli* SP1.1/pKD12.112 synthesized 20.2 g/L of shikimic acid, 4.6 g/L of DHS, and only 1.9 g/L of quinic acid. Under identical conditions SP2.1/pKD12.112 synthesized 37 g/L of shikimic acid, 2.1 g/L of quinic acid and 4.2 g/L of DHS. The decrease in the synthesized titers of shikimic acid is consistent with the known impact of increased D-glucose availability on the concentration and yield of L-phenylalanine synthesized by *E. coli*. Konstantinov, K. B. et al., *J. Ferment. Bioeng.* 70:253 (1990); Konstantinov, K. B. et al., *J. Ferment. Bioeng.* 71:350 (1991). More importantly, improvement of the shikimate:quinate molar ratio from 2.4:1 ($K_c$=0.1) to 11.8:1 ($K_c$=0.8) allowed quinic acid to be completely removed during crystallization of shikimic acid.

TABLE 2

Products Synthesized By *E. coli* SP1.1/pKD12.112 As A Function Of Time And D-glucose Addition Parameters

| | $K_c$ = 0.1 | | | $K_c$ = 0.8 | | |
|---|---|---|---|---|---|---|
| | SA[a] | QA | DHS | SA | QA | DHS |
| 12 h | 1.1 | 0.0 | 0.3 | 1.0 | 0.0 | 0.2 |
| 18 h | 5.3 | 2.5 | 1.2 | 3.1 | 0.0 | 0.6 |
| 24 h | 11.4 | 5.7 | 2.2 | 6.4 | 0.8 | 1.2 |
| 30 h | 17.1 | 8.3 | 2.7 | 10.9 | 1.3 | 2.2 |
| 36 h | 23.1 | 10.8 | 4.2 | 15.7 | 1.8 | 3.5 |
| 42 h | 27.2 | 12.6 | 4.4 | 20.2 | 1.9 | 4.6 |

[a]Concentrations in g/L of shikimic acid (SA), quinic acid (QA), and 3-dehydroshikimic acid (DHS)

Additional fermentation runs resulted in similar yields of shikimic acid and shikimic acid:quinic acid ratios. When the gain ($K_c$) for proportional-integral-derivative control for the glucose feed was set to 0.1, both SP1.1/pKD12.112 and SP2.1/pKD12.112 synthesized unexceptable mixtures of shikimic acid and quinic acid. SP1.1/pKD12.112 achieved a shikimic acid to quinic acid molar ratio of 3.0 while SP2.1/pKD12.112 achieved a molar ratio of 5.0 (Table 3). Attempts to obtain pure shikimic acid from culture broths with molar ratios in this range were unsuccessful. Although synthesis of byproduct DHS represents a loss in shikimic acid titers, DHS is easily separated from shikimic acid during purification. DHS formation was not an obstacle to obtaining pure shikimic acid.

TABLE 3

Summary Of Fermentation Results

| Strain | Modification | $K_c$ | SA[a] (g/L) | QA[a] (g/L) | DHS[a] (g/L) | Molar Ratio SA:QA |
|---|---|---|---|---|---|---|
| SP1.1/pKD12.112 | — | 0.1 | 38.2 | 12.4 | 6.5 | 3.0 |
| SP2.1/pKD12.112 | — | 0.1 | 33.2 | 7.8 | 5.4 | 5.0 |
| SP1.1/pKD12.112 | increase $K_c$ | 0.8 | 20.2[b] | 1.9 | 4.6 | 12 |
| SP2.1/pKD12.112 | increase $K_c$ | 0.8 | 36.6[b] | 2.2 | 4.4 | 18 |
| SP1.1/pKD12.112 | add M αDG (1 mM) | 0.1 | 40.3 | 0 | 5.3 | >40 |
| SP2.1/pKD12.112 | add M αDG (0.5 mM) | 0.1 | 39.6 | 4.1 | 4.8 | 11 |
| SP1.1/pKD12.138 | add M αDG (1 mM); tktA | 0.1 | 51.1 | 4.3 | 8.8 | 13 |
| SP2.1/pKD12.138 | add M αDG (0.5 mM); tktA | 0.1 | did not change phase | | | |

[a]after 48 h of culturing except as noted differently
[b]after 42 h of culturing When the gain controlling the glucose feed was increased from 0.1 to 0.8, significant improvement in the shikimic acid to quinic acid molar ratio was observed. Increasing $K_c$ to 0.8 results in a stronger response by the glucose pump when the dissolved oxygen level deviates from its setpoint. Increased values of $K_c$ therefore result in higher steady-state glucose concentrations in the culture medium. After 42 h of culturing with $K_c$ set at 0.8, SP1.1/pKD12.112 synthesized 20.2 g/L of shikimic acid and only 1.9 g/L of quinic acid to achieve a molar ratio of 12 (Table 3). Comparable improvement was seen with SP2.1/pKD12.112 which achieved a molar ratio of 18 by synthesizing 36.6 g/L of shikimic acid and 2.2 g/L of quinic acid after 42 h (Table 3). Shikimic acid readily purified away from the quinic acid from culture broths in which the molar ratio exceeds approximately 9.

Although increasing $K_c$ effectively suppresses quinic acid formation, these runs are extremely difficult to control. Dissolved oxygens levels oscillate as a direct result of oscillations in glucose feeding rates. These runs must be closely monitored after approximately 36 h into the run in order to avoid large, unnecessary additions of glucose. Since the runs could routinely be nursed along through 42 h but rarely through 48 h without a loss of control, the runs were terminated after 42 h. Increasing the steady-state glucose concentration in the culture broth also had a significant impact on the rate of shikimic acid production for SP1.1/pKD12.112. At the higher gain, SP1.1/pKD12.112 synthesized 20.2 g/L of shikimic acid after 42 h, as compared to 33 g/L at this same time when the gain was set to the lower value. The effect on the rate of production, however, was not observed for SP2.1/pKD12.112.

An alternative to increasing $K_c$ in order to suppress quinic acid formation was addition of a non-hydrolyzable glucose analog to the fermentation broth. Methyl α-D-glucopyranoside (MαDG) was added to the fermentation medium at the time of inoculation and the fermentation was then run without further adjustment. Addition of 1 mM MαDG to the fermentation of SP1.1/pKD12.112 resulted in the synthesis of 40.3 g/L of shikimic acid (Table 3). Quinic acid was not detected. Although several concentrations were examined, 1 mM MαDG was the minimum concentration that afforded complete suppression of quinic acid formation. Addition of MαDG to SP2.1/pKD12.112 cultures also resulted in quinic acid suppression. After 48 h of culturing in the presence of 0.5 mM MαDG, SP2.1/pKD12.112 (Table 3) synthesized 39.6 g/L of shikimic acid and 4.1 g/L of quinic acid, resulting in a molar ratio 11. Higher concentrations of MαDG showed no further improvement in quinic acid suppression.

With conditions established that adequately suppress quinic acid formation without significantly compromising control, attention was turned to increasing shikimic acid titers using transketolase overexpression. When cultured in the presence of 1 mM MαDG, SP1.1/pKD12.138 synthesized 51.1 g/L of shikimic acid and 4.3 g/L of quinic acid, affording a molar ratio exceeding 13 (Table 3). Transketolase expression resulted in a 25% increase in shikimic acid titers while maintaining a molar ratio of shikimic acid to quinic acid that allows shikimic acid isolation. The concentration of DHS byproduct also increased to 8.8 g/L, providing added incentive to obtain a shikimate dehydrogenase insensitive to shikimic acid inhibition. When SP2.1/pKD12.138 was cultured under standard conditions, the fermentation never reached the point of phase change. At 33° C. growth of SP2.1/pKD12.138 was slow and resulted in significant acetate production. A slight increase in culturing temperature would likely increase the rate of growth in order to prevent this situation.

Microbial synthesis of shikimic acid as described herein may supplant isolation of this hydroaromatic from plant sources which has limited shikimic acid's synthetic utility. At the same time; increased availability of shikimic acid may portend wider utilization of this hydroaromatic. The theoretical maximum yield for microbial synthesis of shikimic acid is 43% from D-glucose. Draths, K. M. et al., *J. Am. Chem. Soc.* 117:2395 (1995). Comparison with the yields achieved thus far for microbial synthesis of shikimic acid (14–22%) along with the apparent lack of toxicity of this hydroaromatic toward the microbial biocatalyst suggest that sizable increases in yields and titers are possible. Such improvements coupled with economies of scale associated with large scale fermentation may even extend utilization of shikimic acid from chiral synthon to disposable chirality employable in the manufacture of large-volume aromatic chemicals.

II. Methods

General. For $^1$H NMR quantitation of solute concentrations, solutions were concentrated to dryness under reduced pressure, concentrated to dryness one additional time from $D_2O$, and then redissolved in $D_2O$ containing a known concentration of the sodium salt of 3-(trimethylsilyl)propionic-2,2,3,3-$d_4$ acid (TSP) purchased from Lancaster Synthesis Inc. Concentrations were determined by comparison of integrals corresponding to each compound with the integral corresponding to TSP ($\delta=0.00$ ppm) in the $^1$H NMR. All $^1$H NMR spectra were recorded on a Varian VXR-300 FT-NMR Spectrometer (300 MHz).

Culture Medium. All medium was prepared in distilled, deionized water. M9 salts (1 L) contained $Na_2HPO_4$ (6 g), $KH_2PO_4$ (3 g), NaCl (0.5 g) and $NH_4Cl$ (1 g). M9 minimal medium (1 L) consisted of 1 L of M9 salts containing D-glucose (10 g), $MgSO_4$ (0.12 g), thiamine hydrochloride (0.001 g), L-phenylalanine (0.040 g), L-tyrosine (0.040 g), L-tryptophan (0.040 g), p-hydroxybenzoic acid (0.010 g), potassium p-aminobenzoate (0.010 g), and 2,3-dihydroxybenzoic acid (0.010 g). Ampicillin was added (0.05 g/L) where indicated. Solutions of M9 salts, $MgSO_4$, and glucose were autoclaved individually and then mixed. Aromatic amino acids, aromatic vitamins, and ampicillin were sterilized through 0.22-$\mu$m membranes.

Fermentation medium (1 L) contained $K_2HPO4$ (7.5 g), ammonium iron (III) citrate (0.3 g), citric acid monohydrate (2.1 g), L-phenylalanine (0.7 g), L-tyrosine (0.7 g), L-tryptophan (0.35 g), and concentrated $H_2SO_4$ (1.2 mL). Fermentation medium was adjusted to pH 7.0 by addition of concentrated $NH_4OH$ before autoclaving. The following supplements were added immediately prior to initiation of the fermentation: D-glucose (20 g), $MgSO_4$ (0.24 g), p-hydroxybenzoic acid (0.010 g), potassium p-aminobenzoate (0.010 g), 2,3-dihydroxybenzoic acid (0.010 g), and trace minerals including $(NH_4)_6(Mo_7O_{24})$ 5.4$H_2O$ (0.0037 g), $ZnSO_4.7H_2O$ (0.0029 g), $H_3BO_3$ (0.0247 g), $CuSO_4.5H_2O$ (0.0025 g), and $MnCl_2.4H_2O$ (0.0158 g). D-Glucose and $MgSO_4$ were autoclaved separately while aromatic vitamins and trace minerals were sterilized through 0.22-$\mu$m membranes.

Fermentations. Fermentations employed a 2.0 L working capacity B. Braun M2 culture vessel. Utilities were supplied by a B. Braun Biostat MD that was controlled by a DCU-1. Data acquisition utilized a Dell Optiplex Gs$^+$ 5166M personal computer equipped with B. Braun MFCS/Win software. Temperature, pH, and glucose feeding were controlled with PID control loops. Temperature was maintained at 33° C. pH was maintained at 7.0 by addition of concentrated $NH_4OH$ or 2 N $H_2SO_4$. Dissolved oxygen (D.O.) was measured using a Mettler-Toledo 12 mm sterilizable $O_2$ sensor fitted with an Ingold A-type $O_2$ permeable membrane. D.O. was maintained at 10% air saturation.

Inoculants were started by introduction of a single colony into 5 mL of M9 medium containing ampicillin. The culture was grown at 37° C. with agitation at 250 rpm for 24 h and subsequently transferred to 100 mL of M9 medium containing ampicillin. After growth at 37° C. , 250 rpm for an additional 12 h, the inoculant was ready for transfer into the fermentation vessel. The initial glucose concentration in the fermentation medium was 20 g/L. Three staged methods were used to maintain D.O. levels at 10% air saturation during the course of run. With the airflow at an initial setting of 0.06 L/L/min, D.O. concentration was maintained by increasing the impeller speed from its initial set point of 50 rpm to its preset maximum of 940 rpm. With the impeller constant at 940 rpm, the mass flow controller then maintained D.O. levels by increasing the airflow rate from 0.06 L/L/min to a preset maximum of 1.0 L/L/min. At constant impeller speed and constant airflow rate, D.O. levels were finally maintained at 10% air saturation for the remainder of the fermentation by oxygen sensor-controlled glucose feeding. At the beginning of this stage, D.O. levels fell below 10% air saturation due to residual initial glucose in the medium. This lasted for approximately 1 h before glucose (65% w/v) feeding started. The PID control parameters were set to 0.0 (off) for the derivative control ($\tau_D$) and 999.9 s (minimum control action) for integral control ($\tau_I$). $X_p$ was set to 950% to achieve a $K_c$ of 0.1 and 125% to achieve a $K_c$ of 0.8.

Samples (10 mL) of fermentation broth were taken at 6 h intervals. Cell densities were determined by dilution of fermentation broth with water (1:100) followed by measurement of absorption at 600 nm ($OD_{600}$). Dry cell weight (g/L) was obtained using a conversion coefficient of 0.43 g/L/$OD_{600}$. The remaining fermentation broth was centrifuged for 4 min using a Beckman microcentrifuge to obtain cell-free broth. Solute concentrations in the cell-free broth were determined by $^1$H NMR.

Purification of Shikimic Acid from Fermentation Broth. The fermentation broth (1100–1200 mL) was centrifuged at 14000 g for 20 min and the cells were discarded. The resulting supernatant was refluxed for 4 h, cooled to room temperature, and the pH adjusted to 2.5 by addition of concentrated $H_2SO_4$. After centrifugation at 14000 g for 20 min, a clear yellow solution was poured away from the cellular debris and adjusted to pH 6.9 by addition of concentrated $NH_4OH$. The solution was combined with 5 g of Darco KB-B activated carbon, swirled at 50 rpm for 1–2 h, and then filtered through Whatman 5 filter paper. Filtered material was washed with an additional 250 mL of water. The combined filtrates were then treated in the same way with a second batch of activated carbon.

Following treatment of the solution with carbon, the dark color was less intense than prior to treatment, but the solution was not colorless. Addition of glacial acetic acid to a final concentration of 15% afforded a clear, yellow solution which was then eluted through a column of AG1-x8 (acetate form, 5 cm×20 cm) at 4° C. Following elution of the column with an additional 400 mL of 15% aqueous acetic acid, the combined eluents were passed through a column of Dowex 50 ($H^+$ form, 5 cm×20 cm) at 4° C. which was then washed with 400 mL of 15% aqueous acetic acid. The eluents off the cation exchange column were combined and concentrated to approximately 150 mL by boiling and then to dryness by rotary evaporation, leaving a hard white solid (83% recovery through this step). Recrystallization from a mixture of methanol and ethyl acetate afforded shikimic acid as a fine white powder (61% recovery based on shikimic acid quantified in crude fermentation broth).

The foregoing discussion discloses and describes merely exemplary embodiments of the present invention. One skilled in the art will readily recognize from such discussion, and from the accompanying drawing and claims, that various changes, modifications and variations can be made therein without departing from the spirit and scope of the invention as defined in the following claims.

All references cited herein are incorporated by reference as if fully set forth. In addition, U.S. Ser. No. 09/240,441, now abandoned, entitled "Biocatalytic Synthesis Of Quinic Acid," filed Jan. 29, 1999, is also expressly incorporated by reference.

We claim:

1. A method for the production of shikimic acid from a carbon source comprising:
  a) providing a microbe selected from the group consisting of bacteria, fungi and yeast, wherein the microbe comprises one or more enzyme-encoding recombinant DNA molecules, wherein the encoded enzyme is selected from the group consisting of 3-deoxy-D-arabino-heptulosonic acid 7-phosphate synthase, 3-dehydroquinate synthase, 3-dehydroquinate dehydratase, and 3-dehydroshikimate dehydrogenase, and wherein the microbe further comprises an inactivating mutation in at least one DNA molecule which encodes a shikimate kinase isozyme; and
  b) culturing said microbe in the presence of the carbon source.

2. The method of claim 1, wherein the microbe is *E. coli*.

3. The method of claim 1, wherein the microbe comprises a recombinant DNA encoding shikimate dehydrogenase and a recombinant DNA encoding 3-dehydroquinate synthase.

4. The method of claim 3, wherein the recombinant DNA encoding shikimate dehydrogenase comprises an *E. coli* aroE.

5. The method of claim 4, wherein the aroE is contained in a plasmid.

6. The method of claim 5, wherein the plasmid is pKD12.112.

7. The method of claim 5, wherein the plasmid is pKD12.138.

8. The method of claim 3, wherein the recombinant DNA encoding 3-dehydroquinate synthase comprises an *E. coli* aroB.

9. The method of claim 8, wherein the microbe further comprises the aroB as an insertion into an *E. coli* serA.

10. The method of claim 1, wherein the inactivyating mutation in at least one DNA molecule which encodes a shikimate kinase isozyme comprises a deletion mutation in either or both of an *E. coli* aroK and an *E. coli* aroL.

11. The method of claim 1, wherein the microbe comprises a recombinant DNA encoding a 3-deoxy-D-arabino-heptulosonate-7-phosphate synthase insensitive to feedback inhibition by aromatic amino acids.

12. The method of claim 11, wherein the recombinant DNA encoding a 3-deoxy-D-arabino-heptulosonate-7-phosphate synthase insensitive to feedback inhibition by aromatic amino acids is an *E. coli* aroF$^{FBR}$.

13. The method of claim 1, wherein the carbon source is glucose.

14. The method of claim 1, wherein the cells are cultured in the presence of a carbon source and a non-hydrolyzable glucose analog.

15. The method of claim 14, wherein the non-hydrolyzable glucose analog is methyl glucopyranoside.

16. The method of claim 15, wherein the methyl glucopyranoside is present in an amount of from about 0.5 mM to about 1.0 mM.

17. A method for the production of shikimic acid from a carbon source comprising:
  a) providing a microbe selected from the group consisting of bacteria, fungi and yeast, wherein the microbe comprises one or more enzyme-encoding recombinant DNA molecules, wherein the encoded enzyme is selected from the group consisting of 3-deoxy-D-arabino-heptulosonic acid 7-phosphate synthase, 3-dehydroquinate synthase, 3-dehydroquinate dehydratase, and 3-dehydroshikimate dehydrogenase, and wherein the microbe further comprises an inactivating mutation in at least one DNA molecule which encodes a shikimate kinase isozyme; and
  b) culturing said microbe in the presence of an amount of the carbon source whereby the molar ratio of shikimic acid to quinic acid is greater than about 9.

18. The method of claim 17, wherein the microbe is *E. coli*.

19. The method of claim 17, wherein the microbe comprises a recombinant DNA encoding shikimate dehydrogenase and a recombinant DNA, encoding 3-dehydroquinate synthase.

20. The method of claim 19, wherein the recombinant DNA encoding shikimate dehydrogenase comprises an *E. coli* aroE.

21. The method of claim 20, wherein the DNA molecule encoding shikimate dehydrogenase (aroE) is contained in a plasmid.

22. The method of claim 21, wherein the plasmid is pKD12.112.

23. The method of claim 21, wherein the plasmid is pKD12.138.

24. The method of claim 19, wherein the recombinant DNA encoding 3-dehydroquinate synthase is an *E. coli* aroB.

25. The method of claim 24, wherein the microbe further comprises the aroB as an insertion into an *E. coli* serA.

26. The method of claim 17, wherein the inactivating mutation in at least one DNA molecule which encodes a shikimate kinase isozyme comprises a deletion mutation in either or both of an *E. coli* aroK and an *E. coli* aroL.

27. The method of claim 17, wherein the microbe comprises a recombinant DNA encoding a 3-deoxy-D-arabino-heptulosonate-7-phosphate synthase insensitive to feedback inhibition by aromatic amino acids.

28. The method of claim 17, wherein the recombinant DNA encoding a 3-deoxy-D-arabino-heptulosonate-7-phosphate synthase insensitive to feedback inhibition by aromatic amino acids is an *E. coli* aroF$^{FBR}$.

29. The method of claim 17, wherein the carbon source is glucose.

30. A method for the production of shikimic acid from a carbon source comprising:
   a) providing a microbe selected from the group consisting of bacteria, fungi and yeast, wherein the microbe comprises one or more enzyme-encoding recombinant DNA molecules, wherein the enzyme is selected from the group consisting 3-deoxy-D-arabino-heptulosonic acid 7-phosphate synthase, 3-dehydroquinate synthase, 3-dehydroquinate dehydratase, and 3-dehydroshikimate dehydrogenase; and
   b) culturing said microbe in the presence of the carbon source and a non-hydrolyzable glucose analog, whereby the molar ratio of shikimic acid to quinic acid is greater than about 9.

31. The method of claim 30, wherein the microbe is *E. coli*.

32. The method of claim 30, wherein the microbe comprises a recombinant DNA encoding shikimate dehydrogenase and a recombinant DNA encoding 3-dehydroquinate synthase.

33. The method of claim 32, wherein the recombinant DNA encoding shikimate dehydrogenase comprises an *E. coli* aroE.

34. The method of claim 33, wherein the DNA molecule encoding shikimate dehydrogenase (aroE) is contained in a plasmid.

35. The method of claim 34, wherein the plasmid is pKD12.112.

36. The method of claim 34, wherein the plasmid is pKD12.138.

37. The method of claim 32, wherein the 3-dehydroquinate synthase comprises an *E. coli* aroB.

38. The method of claim 37, wherein the microbe further comprises the aroB as an insertion into an *E. coli* serA.

39. The method of claim 30, wherein the microbe comprises a recombinant DNA encoding a 3-deoxy-D-arabino-heptulosonate-7-phosphate synthase insensitive to feedback inhibition by aromatic amino acids.

40. The method of claim 39, wherein the recombinant DNA encoding a 3-deoxy-D-arabino-heptulosonate-7-phosphate synthase insensitive to feedback inhibition by aromatic amino acids is an *E. coli* aroF$^{FBR}$.

41. The method of claim 30, wherein the non-hydrolyzable glucose analog is methyl glucopyranoside.

42. The method of claim 41, wherein the methyl glucopyranoside is present in an amount of from about 0.5 mM to about 1.0 mM.

* * * * *

UNITED STATES PATENT AND TRADEMARK OFFICE
CERTIFICATE OF CORRECTION

PATENT NO. : 6,613,552 B1
DATED : September 2, 2003
INVENTOR(S) : John W. Frost, Karen M. Frost and David Knop It is certified that error appears in the above-identified patent and that said Letters Patent is hereby corrected as shown below:

Column 1,
Line 19, ";" should be -- , --.
Line 24, "Kim." should be -- Kim, --.
Line 67, "material," should be -- material --.

Column 2,
Lines 4 and 11, "drawing" should be -- drawings --.

Column 3,
Line 2, "arok" should be -- aroK --.

Column 7,
Line 2, "*Klebsielia*" should be -- *Klebsiella* --.

Column 8,
Line 65, "oxygens" should be -- oxygen --.

Column 9,
Line 8, "after42 h" should be -- after 42 h --.

Column 10,
Line 34, "5.4H$_2$O" should be --5•4H$_2$O--.
Line 34, "ZnSO$_4$.7H$_2$O" should be --ZnSO$_4$•7H$_2$O--.
Line 35, "CuSO$_4$.5H$_2$O" should be --CuSO$_4$•5H$_2$O--.
Line 35, "MnCl$_2$.4H$_2$O" should be --MnCl$_2$•4H$_2$O--.

Column 11,
Line 54, "drawing" should be -- drawings --.

Column 12,
Line 30, "inactivyating" should be -- inactivating --.

UNITED STATES PATENT AND TRADEMARK OFFICE
CERTIFICATE OF CORRECTION

PATENT NO.     : 6,613,552 B1
DATED          : September 2, 2003
INVENTOR(S)    : John W. Frost, Karen M. Frost and David Knop It is certified that error appears in the above-identified patent and that said Letters Patent is hereby corrected as shown below:

Column 13,
Line 42, after "consisting" insert -- of --.

Signed and Sealed this

Eighteenth Day of January, 2005

JON W. DUDAS
*Director of the United States Patent and Trademark Office*

UNITED STATES PATENT AND TRADEMARK OFFICE
CERTIFICATE OF CORRECTION

PATENT NO. : 6,613,552 B1
DATED : September 2, 2003
INVENTOR(S) : John W. Frost et al.

It is certified that error appears in the above-identified patent and that said Letters Patent is hereby corrected as shown below:

<u>Column 4,</u>
Line 9, Table 1. d), "3-dehydroshikimate" should be -- shikimate --.

<u>Column 12,</u>
Lines 6 and 61, "3-dehydroshikimate" should be -- shikimate --.

<u>Column 14,</u>
Line 3, "3-dehydroshikimate" should be -- shikimate --.

Signed and Sealed this

Twenty-sixth Day of July, 2005

JON W. DUDAS
*Director of the United States Patent and Trademark Office*